United States Patent [19]

Hall

[11] Patent Number: 4,610,812

[45] Date of Patent: * Sep. 9, 1986

[54] USES OF METHYL PHENYL PENTANOL DERIVATIVES IN AUGMENTING OR ENHANCING THE AROMA OR TASTE OF CONSUMABLE MATERIALS

[75] Inventor: John B. Hall, Rumson, N.J.

[73] Assignee: International Flavors & Fragrances Inc., New York, N.Y.

[*] Notice: The portion of the term of this patent subsequent to Jul. 10, 2001 has been disclaimed.

[21] Appl. No.: 784,059

[22] Filed: Oct. 4, 1985

Related U.S. Application Data

[62] Division of Ser. No. 681,656, Dec. 14, 1984.

[51] Int. Cl.⁴ .............................................. C11B 9/00
[52] U.S. Cl. ............................. 252/522 R; 560/254; 568/715
[58] Field of Search .................. 252/522 R; 560/254; 568/715, 814; 131/276

[56] References Cited

U.S. PATENT DOCUMENTS 3,879,425  4/1975  Hall et al. ................. 252/522 R
4,458,699  7/1984  Schreck et al. ................ 131/276

FOREIGN PATENT DOCUMENTS 3103268  8/1982  Fed. Rep. of Germany ...... 568/425

OTHER PUBLICATIONS

Schreck et al., "Chemical Abstracts", vol. 101, (1984), p. 167542.

Primary Examiner—Werren B. Lone
Attorney, Agent, or Firm—Arthur L. Liberman

[57] ABSTRACT

Described are 2-methyl-4-phenyl-1-pentanol derivatives defined according to the structure:

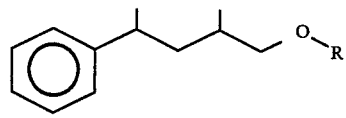

wherein R represents hydrogen or acetyl and uses thereof in augmenting or enhancing the aroma or taste of consumable materials including perfume compositions, colognes, perfumed articles, foodstuffs, chewing gums, medicinal products and chewing tobaccos.

7 Claims, 10 Drawing Figures

GLC PROFILE FOR EXAMPLE I.

GLC PROFILE FOR EXAMPLE I.

NMR SPECTRUM FOR EXAMPLE I.

FIG. 5 NMR SPECTRUM FOR EXAMPLE III

IR SPECTRUM FOR EXAMPLE III.

FIG. 7 NMR SPECTRUM FOR EXAMPLE IV

IR SPECTRUM FOR EXAMPLE IV.

USES OF METHYL PHENYL PENTANOL DERIVATIVES IN AUGMENTING OR ENHANCING THE AROMA OR TASTE OF CONSUMABLE MATERIALS

This is a divisional of application Ser. No. 681,656, filed Dec. 14, 1984.

BACKGROUND OF THE INVENTION

The present invention provides methyl phenyl pentanol derivatives defined according to the generic structure:

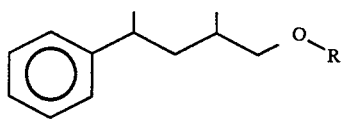

wherein R represents hydrogen or acetyl, an economical process directed towards synthesizing said methyl phenyl pentanol derivatives and organoleptic uses thereof for augmenting or enhancing the aroma or taste of perfume compositions, colognes, perfumed articles, foodstuffs, chewing gums, toothpastes, medicinal products and chewing tobaccos.

There has been considerable work performed relating to substances which can be used to impart (or alter, modify or enhance) fragrances and aromas and/or tastes to (or in) perfume compositions, colognes, perfumed articles, foodstuffs, chewing gums, chewing tobaccos, medicinal products and toothpastes. These substances are used to diminish the use of natural materials, some of which may be in short supply and/or to provide more uniform properties in the finished product.

Powerful, long-lasting, stable green, grapefruit-like, nootkatone-like, animalic, leathery, vetiver-like, olibanum, musky and floral aromas are highly desirable to many types of perfume compositions, perfumes and perfumed articles, particularly herbal fragrances and herbal fragranced soaps and detergents.

Floral, green, weedy, fruity, grapefruit, galbanum-like, nootkatone-like, oriental and green pepper-like aroma and taste nuances are highly desirable in the creation of flavors for foodstuffs, chewing gums, toothpastes, medicinal products and chewing tobaccos.

Methyl phenyl pentanol derivatives are known for use in augmenting or enhancing the aroma of perfume compositions, perfumed articles and colognes. Thus, U.S. Pat. No. 4,206,090 issued on June 3, 1980 discloses the compound having the structure:

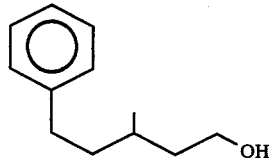

for use in augmenting or enhancing the "rose" aroma of perfume compositions, colognes and perfumed articles. This compound is also disclosed in Beilstein Vol. E III 6(1997) at H6, 551. Other homologues and isomers of methyl phenyl pentanol derivatives also are known to have rosy fragrance aroma nuances. These methyl phenyl pentanol derivatives known in the prior art have the structure:

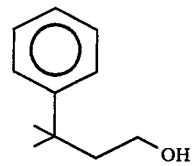

(at Chem. Abstracts 58 2420d and 60 15711a); the structure:

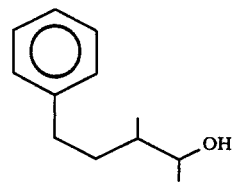

(at Chem. Abstracts 78 42690r (abstract of article by Khalaf in the Journal of Organic Chemistry); the structure:

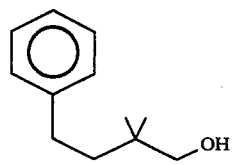

(at Chem. Abstracts 76 126027b (1976) abstract of article by Winstein in J. Org. Chem.); the structure:

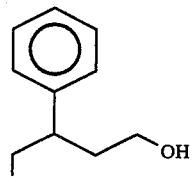

disclosed in Dutch Patent No. 59422; the structures:

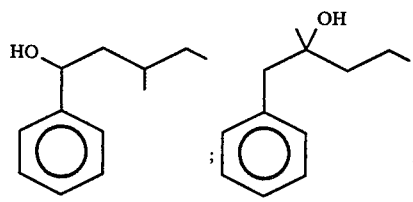

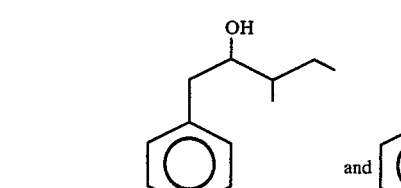

disclosed in Beilstein E III 6 (1997) at H6-551; and the structure:

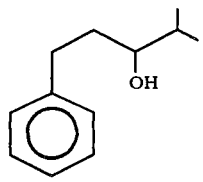

disclosed in Beilstein E III b-1998 at H6 551-2 which is an abstract of Bogert et al JACS 56 (1934) 959 et seq.

German Offenlegungsschrift No. 3,103,268 published on Aug. 26, 1982 discloses the compound having the structure:

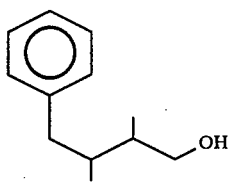

prepared from the precursor compounds having the structures:

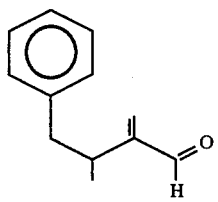 and 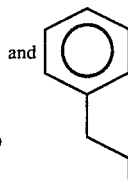

German Offenlegungsschrfit No. 3,103,268 is abstracted at Chem.Abstracts, Volume 97:181968t (1982).

The subject matter of the instant application is disclosed in U.S. Pat. No. 4,458,699 issued on July 10, 1984 and filed on Feb. 11, 1982 as application for U.S. Letters Patent, Ser. No. 347,995. The subject matter claimed herein was conceived of and reduced to practice prior to the filing date of said U.S. Pat. No. 4,458,699, that is, prior to Feb. 11, 1982.

None of the methyl phenyl pentanol derivatives of the prior art have aroma or taste profiles even remotely similar to the aroma or taste profiles of the methyl phenyl pentanol derivatives of the instant application defined according to the structure:

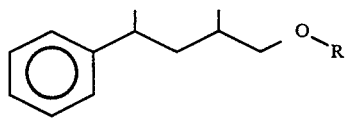

wherein R is hydrogen or acetyl. The methyl phenyl pentanol derivatives of my application defined according to the structure:

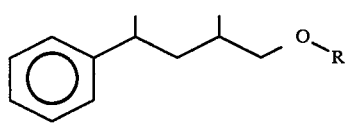

have unexpected, unobvious and advantageous organoleptic properties compared with the methyl phenyl pentanols of the prior art.

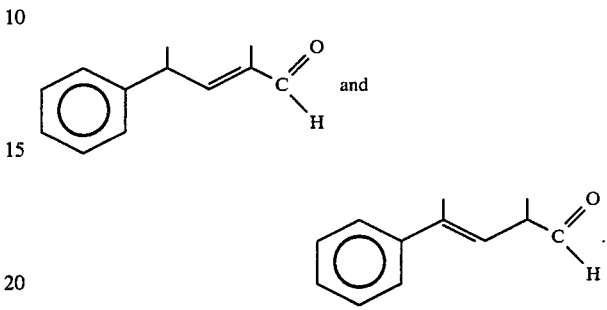

Figure 2:
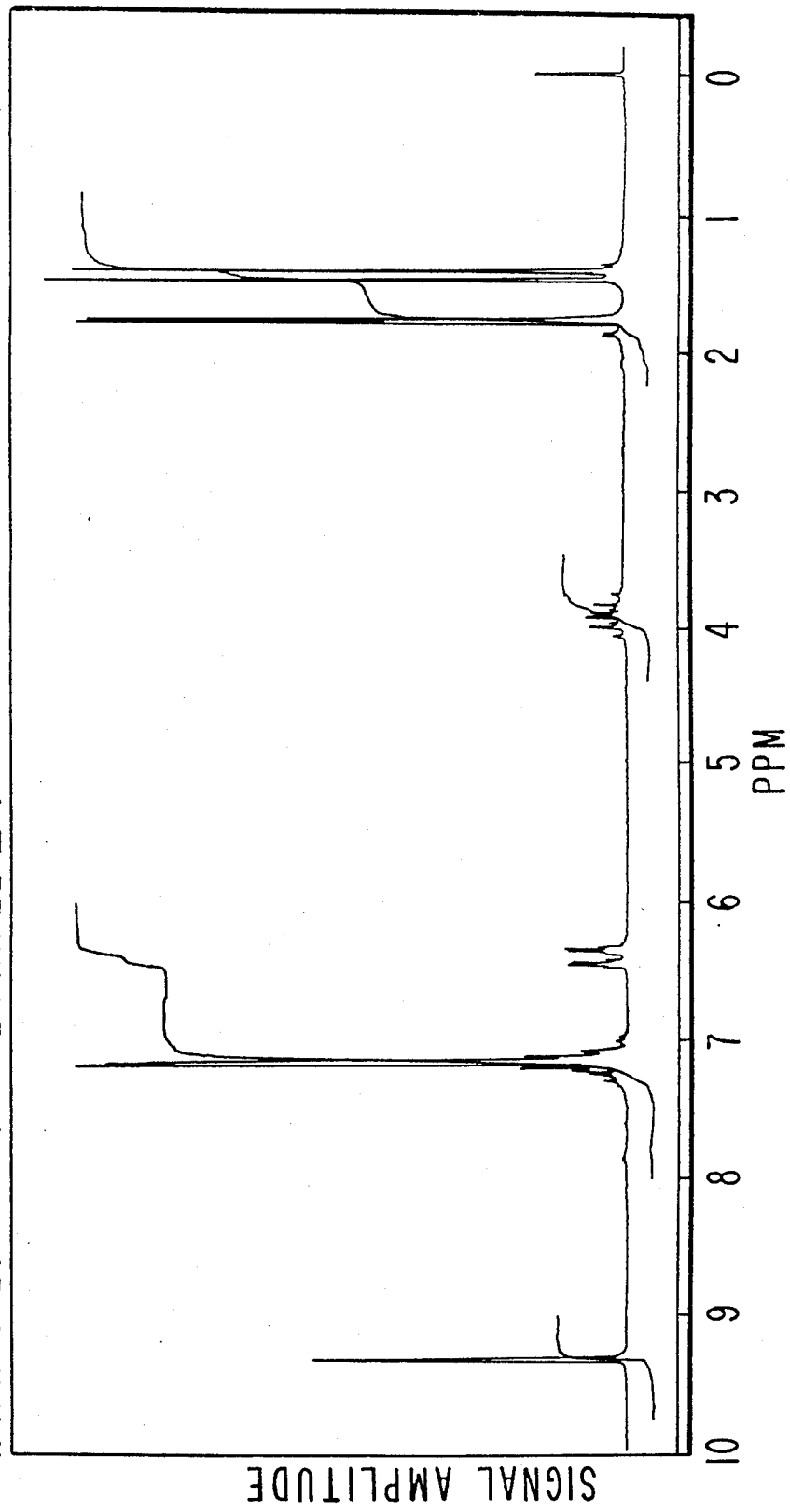

FIG. 2 is the NMR spectrum for the reaction product of Example I containing the compounds having the structures:

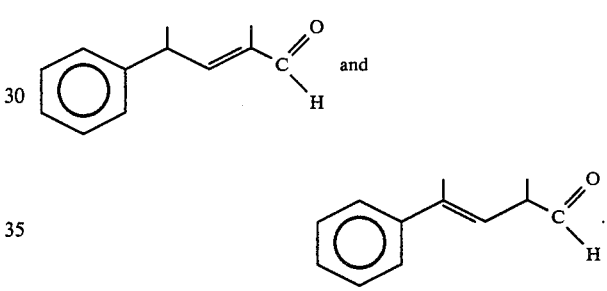

Figure 3:
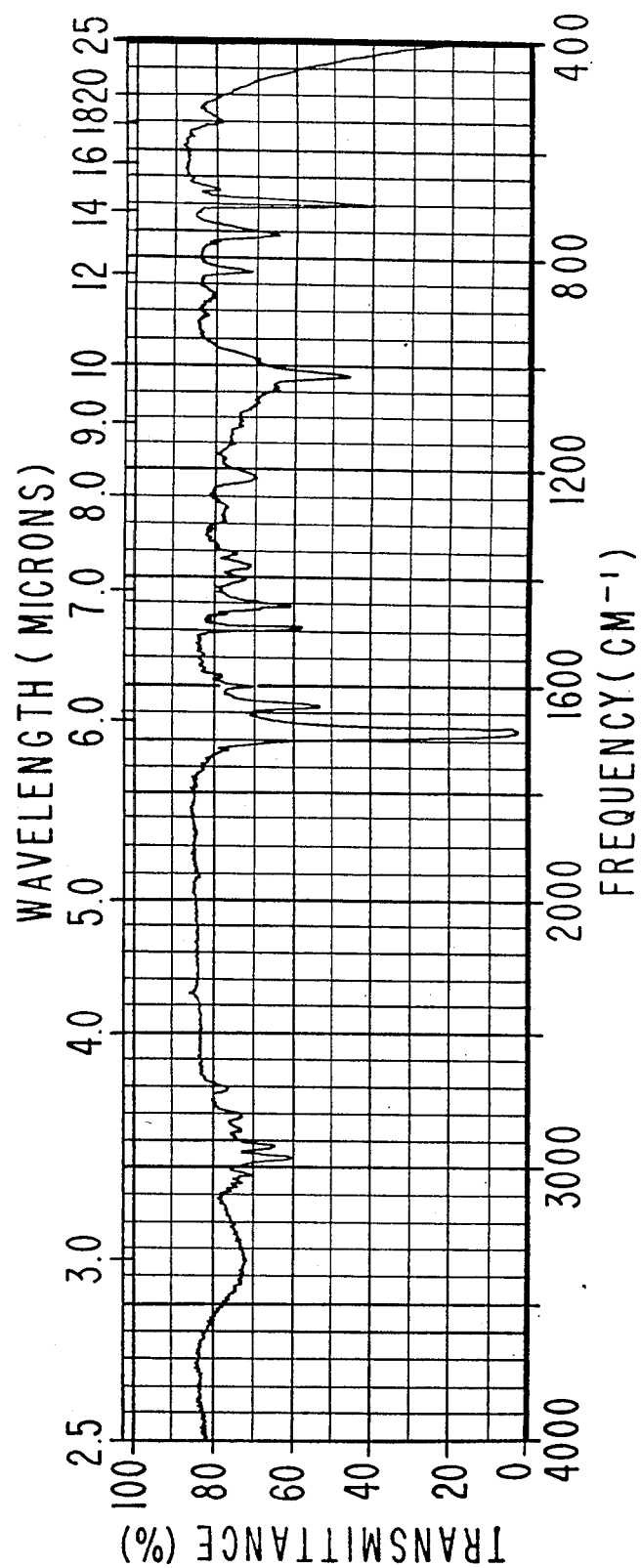

FIG. 3 is the infra-red spectrum for the reaction product of Example I containing the compounds having the structures:

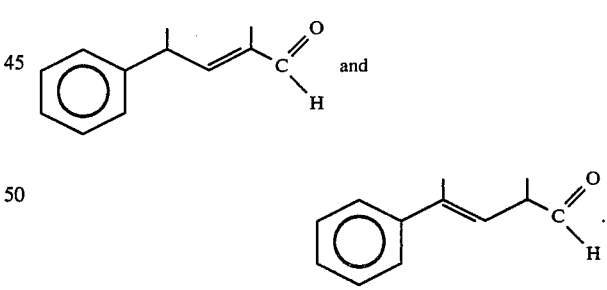

Figure 4:
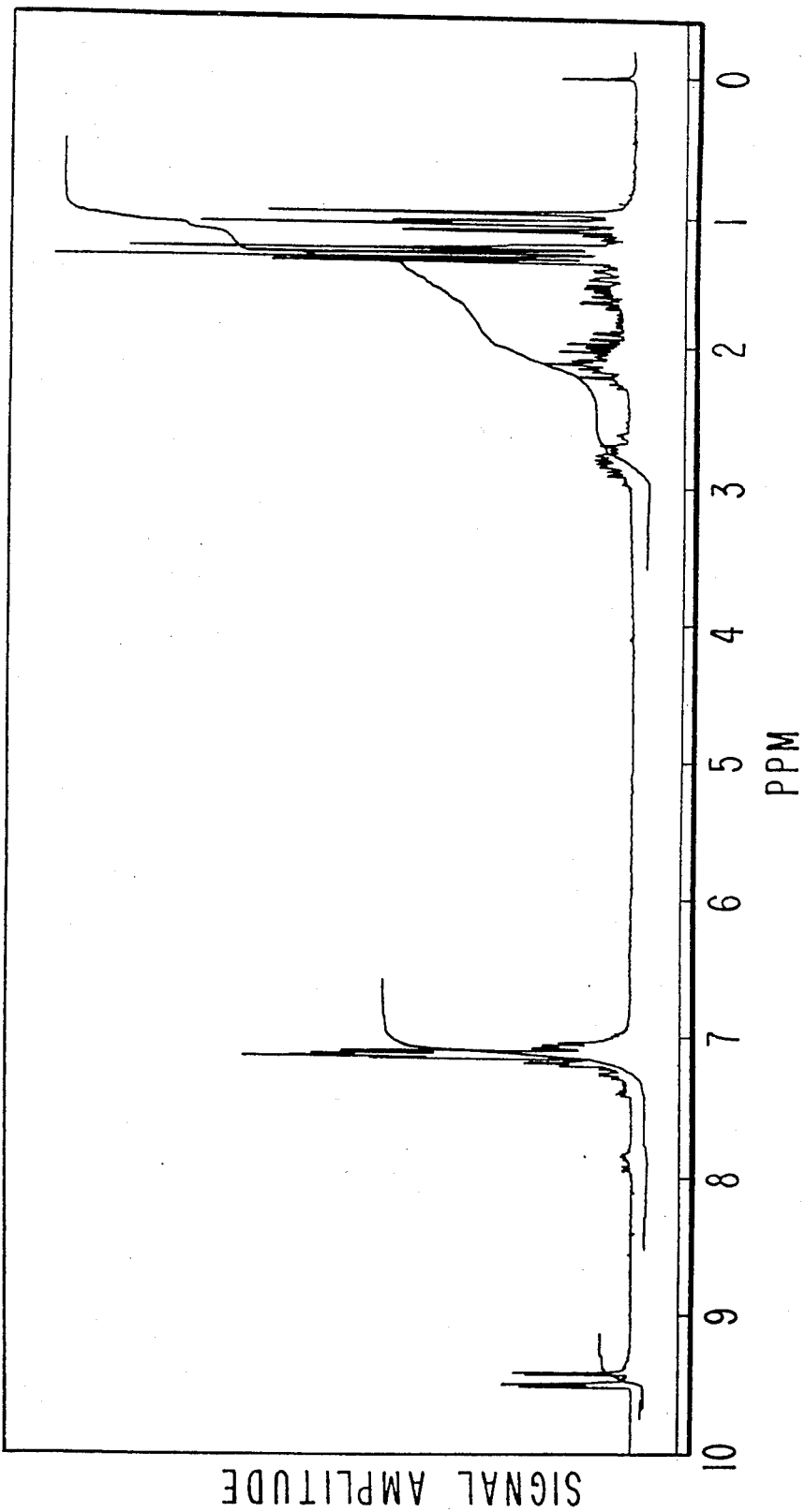

FIG. 4 is the NMR spectrum for the reaction product of Example II which is the compound defined according to the structure:

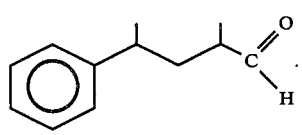

Figure 5:
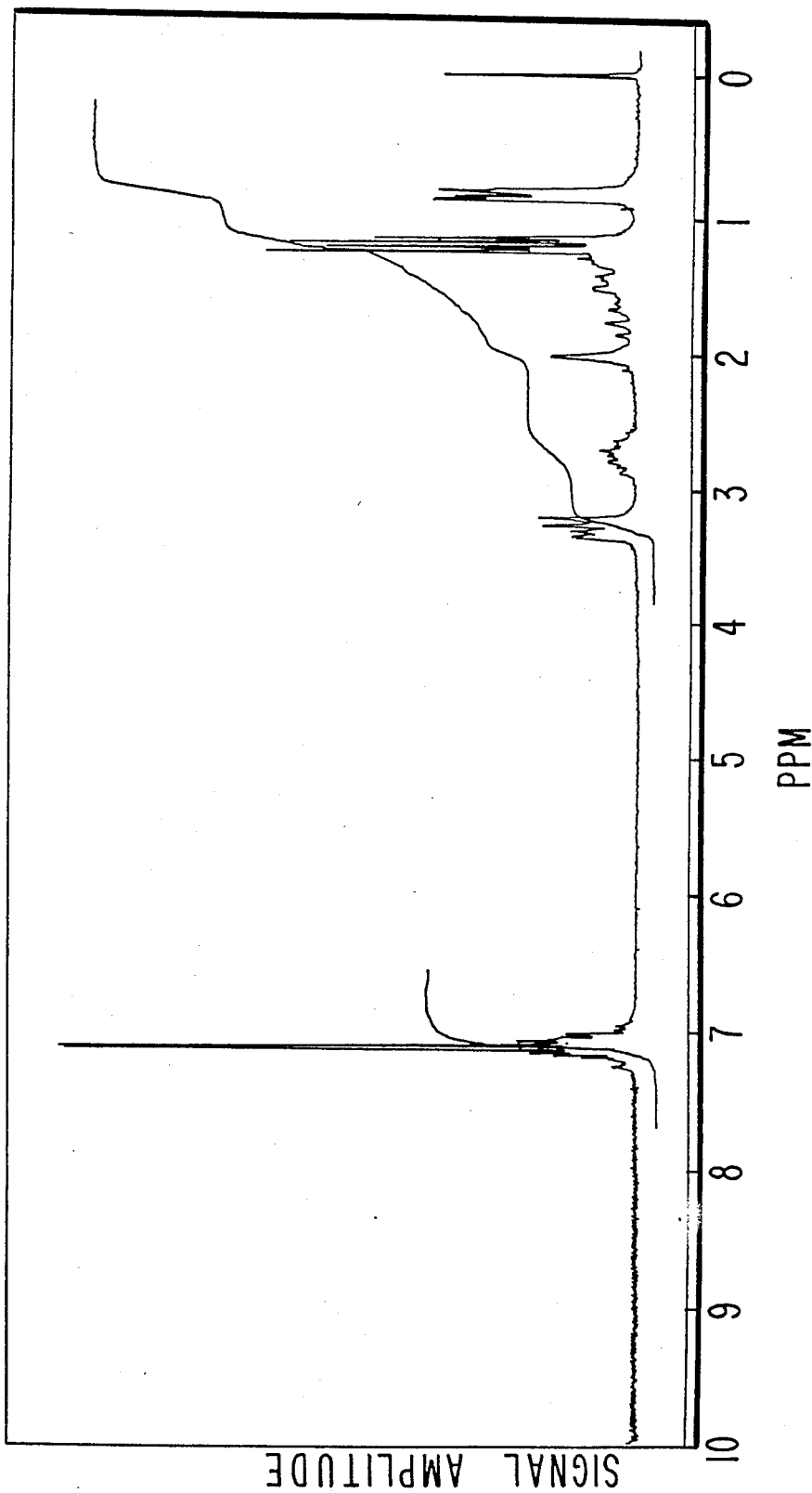

FIG. 5 is the NMR spectrum for the reaction product of Example III containing the compound defined according to the structure:

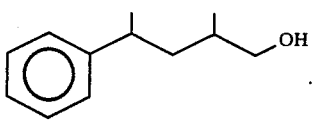

Figure 6:
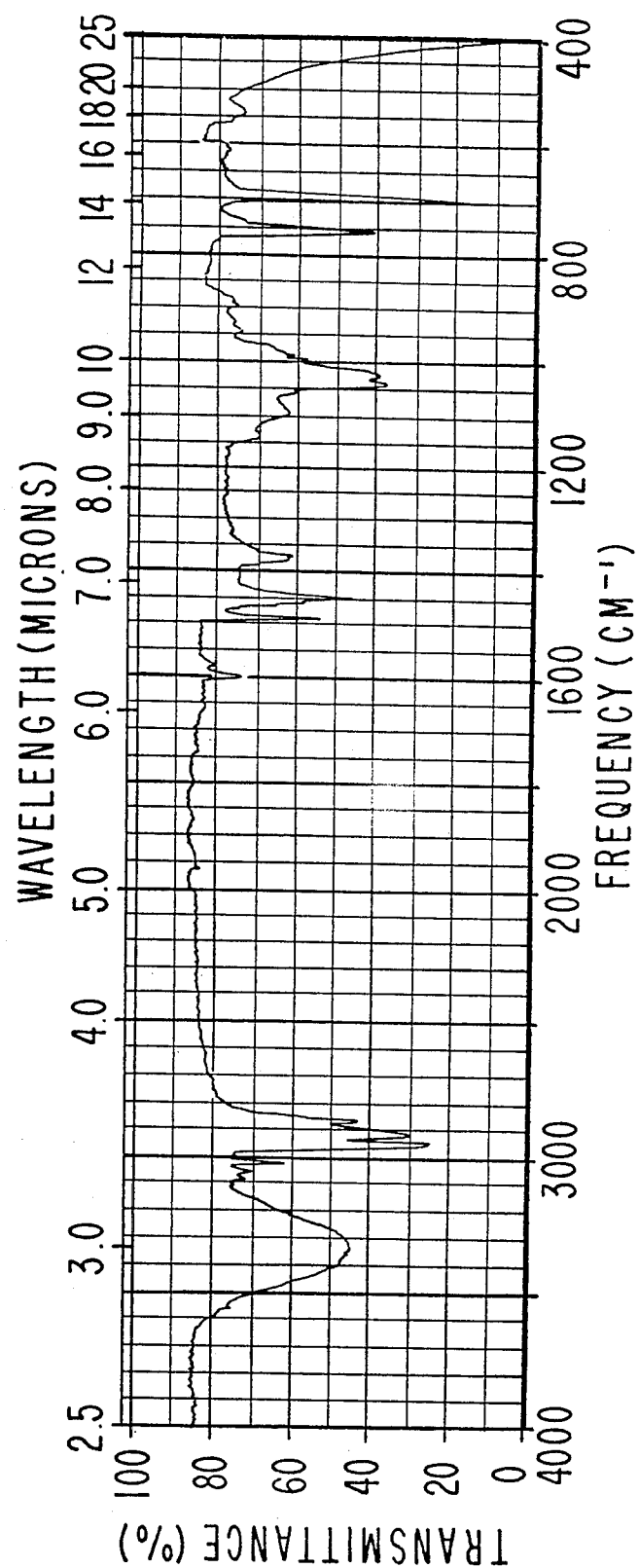

FIG. 6 is the infra-red spectrum for the reaction product of Example III containing the compound having the structure:

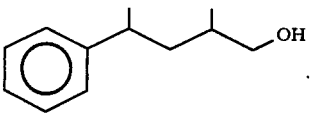

Figure 7:
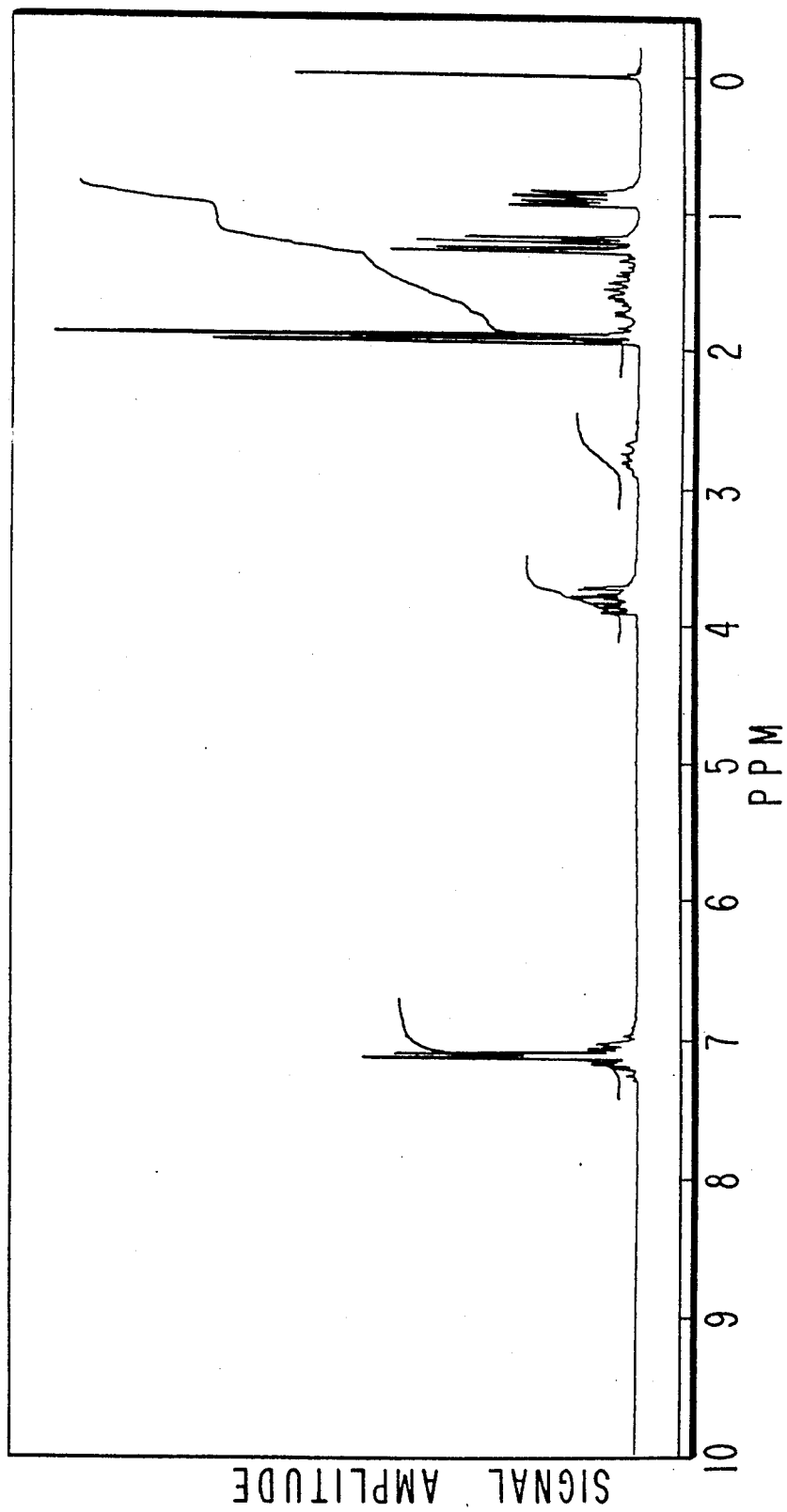

FIG. 7 is the NMR spectrum for the reaction product of Example IV containing the compound having the structure:

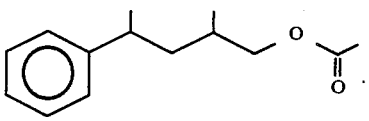

Figure 8:
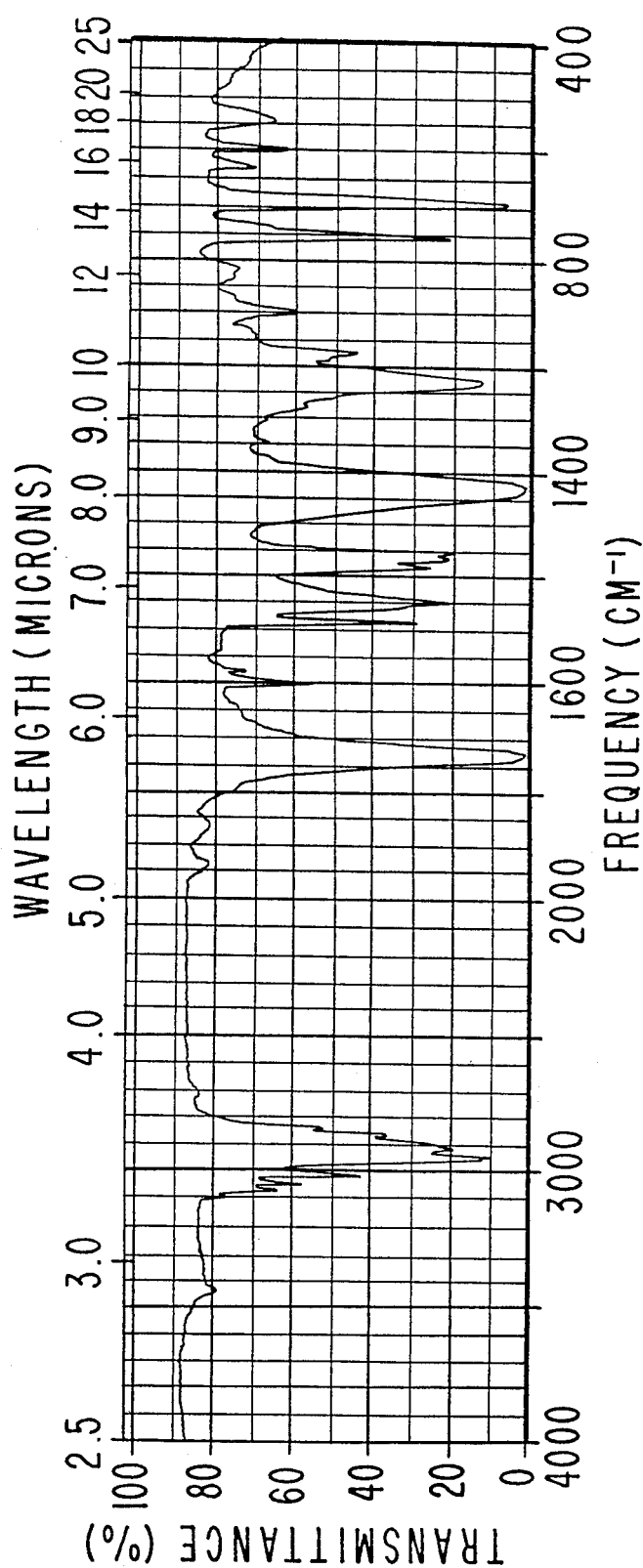

FIG. 8 is the infra-red spectrum for the reaction product of Example IV containing the compound having the structure:

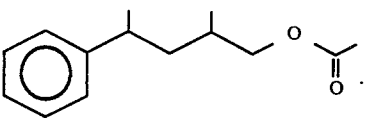

Figure 9:
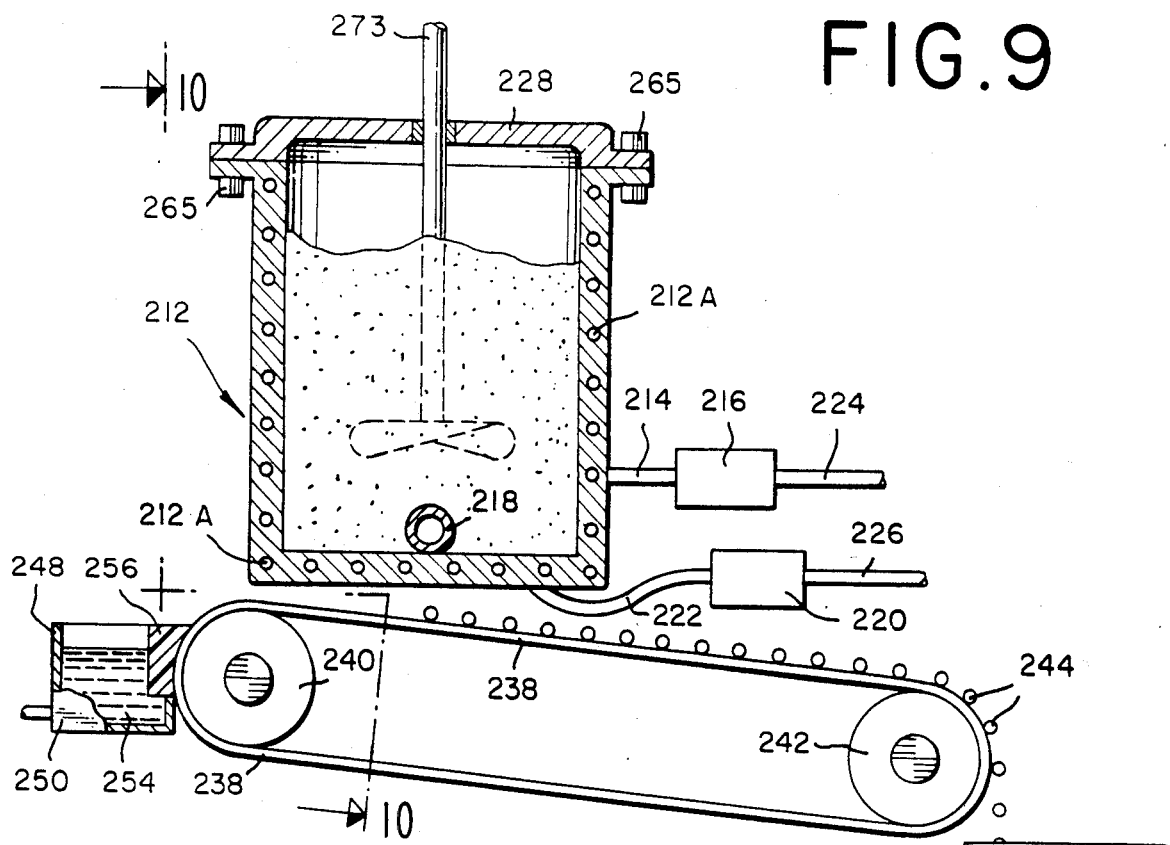

FIG. 9 is a cut-away side elevation view of apparatus used in preparing the fragrance containing polymers of our invention.

Figure 10:
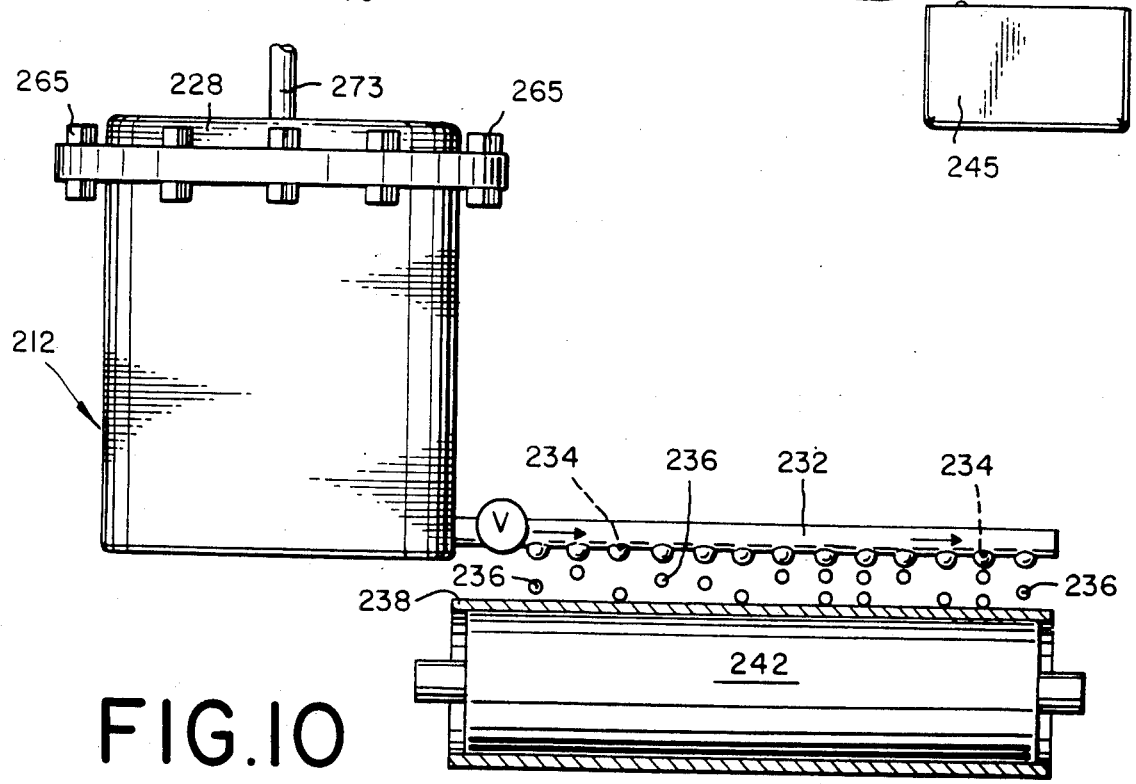

FIG. 10 is a cross-sectional view taken along lines 10—10 of FIG. 9.

DETAILED DESCRIPTION OF THE DRAWINGS

FIGS. 9 and 10 illustrate a preferred method for preparing compositions for the practice of our invention. A thermoplastic polymer, e.g., polyethylene is heated to about 220°–250° F. in a container 212 of the kind illustrated in FIGS. 9 and 10. A formulation containing at least one of the methyl phenyl pentanol derivatives of our invention is then quickly added to the liquified thermoplastic polymer. The lid 228 is put in place and the agitating means 273 is actuated. The temperature is maintained at about 225° F. and the mixing is continued for about 5–15 minutes. The valve "V" is then opened to allow flow of the molten thermoplastic polymer enriched with the fragrance containing the methyl phenyl pentanol derivatives to exit through the orifices 234. The liquid falling through the orifices 234 solidifies almost instantaneously upon impact with moving cooled conveyor 238. The thermoplastic polymer beads or pellets 224 having pronounced aromas which are aesthetically pleasing are thus formed.

The conveyor 238 is moved using conveyor rollers 240 and 242. The vessel 212 is heated using heating coils 212A using power input supplies indicated by reference numerals 214, 216, 224, 222, 220 and 226. The solidified beads containing fragrance containing methyl phenyl pentanol derivatives are indicated by 244 traveling into container 245 where they are used for subsequent processing. The conveyor is cooled using a cooling device indicated by reference numerals 248, 256, 215 and 254.

THE INVENTION

This invention relates to compounds defined according to the structure:

wherein R is hydrogen or acetyl, processes for preparing same as well as uses thereof in augmenting or enhancing the aroma or taste of consumable materials. Such consumable materials are perfume compositions, perfumes, colognes, foodstuffs, chewing gums, chewing tobaccos, medicinal products and toothpastes. This invention also relates to processes for preparing such compounds defined according to the structure:

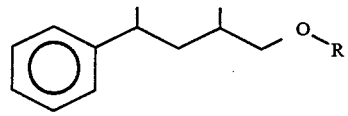

wherein R is hydrogen or acetyl by reacing n-propanol having the structure:

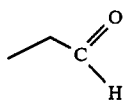

with hydrotropaldehyde having the structure:

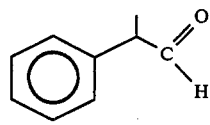

in order to form a mixture of compounds defined according to the structures:

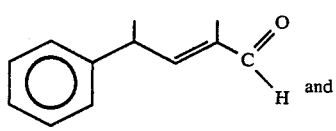 and

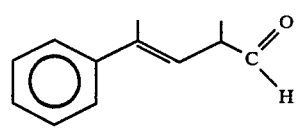

and then reacting this mixture with hydrogen in the presence of a Raney nickel catalyst according to the reactions:

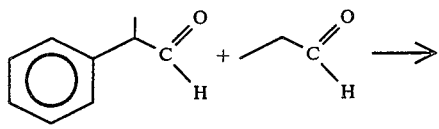

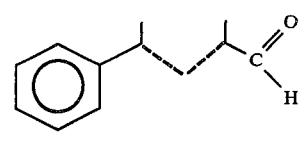

and

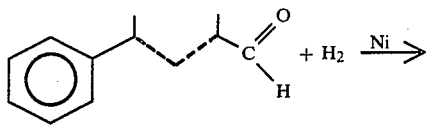

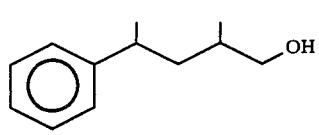

wherein in the above mentioned mixtures, one of the dashed lines is a carbon-carbon double bond and the other of the dashed lines is a carbon-carbon single bond. The resulting compound defined according to the structure:

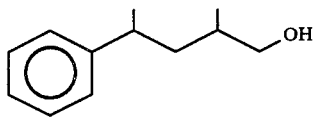

may be further reacted with acetic anhydride according to the reaction:

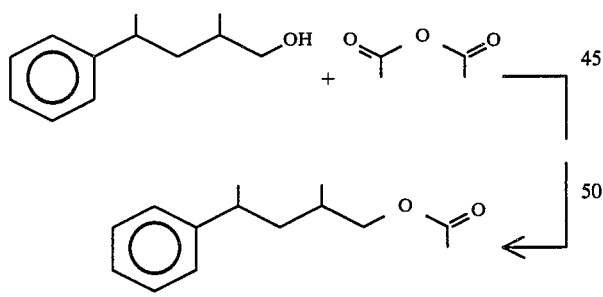

whereby the compound having the structure:

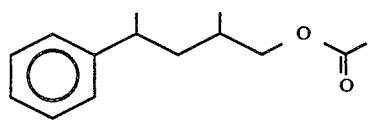

is formed.

Solid and liquid fragrance materials having powerful, long-lasting and stable green, grapefruit-like, nootkatone-like, animalic, leathery, vetiver-like, olibanum, musky and floral aroma nuances may be prepared by the utilization of the methyl phenyl pentanol derivatives defined according to the structure:

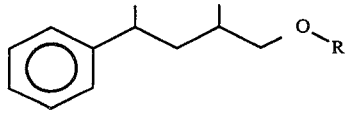

wherein R is hydrogen or acetyl according to our invention.

Solid and liquid foodstuff, medicinal product, chewing gum, chewing tobacco and toothpaste compositions having floral, green, weedy, fruity, grapefruit, galbanum-like, nootkatone-like, oriental and green pepper-like aroma and taste nuances may be provided by the utilization of the compounds defined according to the structure:

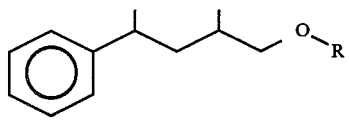

wherein R is hydroge or acetyl according to our invention.

Specifically, the reaction of our invention involves the steps of:

(a) first reacting n-propanol having the structure:

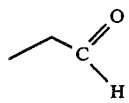

with hydrotropaldehyde having the structure:

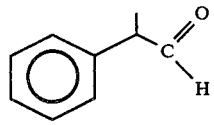

in the presence of a basic catalyst such as sodium hydroxide, potassium hydroxide, lithium hydroxide or barium hydroxide and in the presence of an inert solvent such as methanol, isopropanol or ethanol according to the reaction step:

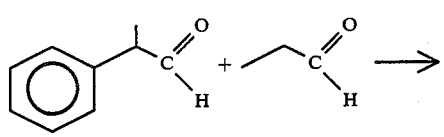

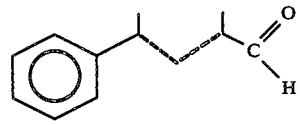

The reaction may take place at temperatures between 15° C. and 100° C. at pressures up to 10 atmospheres. Most preferably and conveniently, the reaction takes place at about 20° C. and 1 atmosphere pressure. At the end of the reaction, the reaction mass is appropriately "worked-up" as by washing the reaction product and then fractionally distilling the resulting reaction product at a vapor temperature in the range of 100°–108° C. at 2 mm/Hg pressure.

(b) The next reaction is that of reacting the mixture of compounds having the structures:

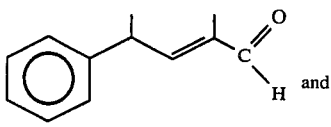 and

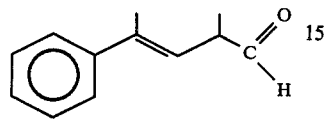

with hydrogen in the presence of a Raney nickel catalyst according to the reaction:

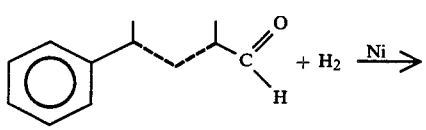

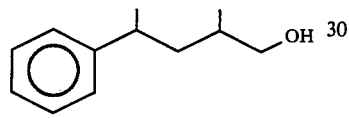

wherein in the mixture of compounds, one of the dashed lines is a carbon-carbon double bond and the other of the dashed lines is a carbon-carbon single bond. The hydrogenation reaction most preferably is carried out in the presence of a solvent which is inert (non-reactive) such as isopropyl alcohol, hexane or ethanol. When such a solvent is used, it is preferred that the mole ratio of solvent:alcohol reactant be approximately 1:1. The percentage of Raney nickel catalyst in the reaction mass may vary from about 3% up to about 10% with a percentage of catalyst of about 5% being preferred. The pressure of hydrogen over the reaction mass may vary from about 50 psig up to about 300 psig with a preferred pressure being 130–200 psig. Pressures greater than the upper limit set forth supra may be used without any decrease in reaction time or increase in yield or conversion. At the end of the hydrogenation reaction, the reaction mass is filtered in order to separate the catalyst from the desired product and the filtrate is distilled using a fractional distillation column operated under vacuum. The distillation of product defined according to the structure:

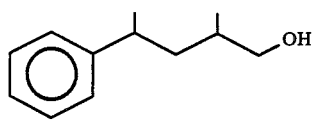

may be carried out at a vapor temperature in the range of 92°–115° C. and a pressure of 1.0–4.0 mm/Hg.

(c) If desired, the resulting alcohol having the structure:

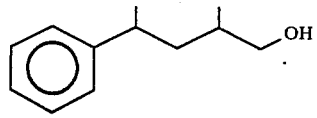

may be esterified with acetic anhydride to form the ester having the structure:

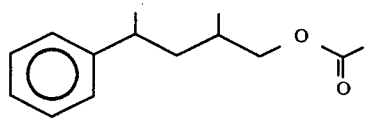

according to the reaction:

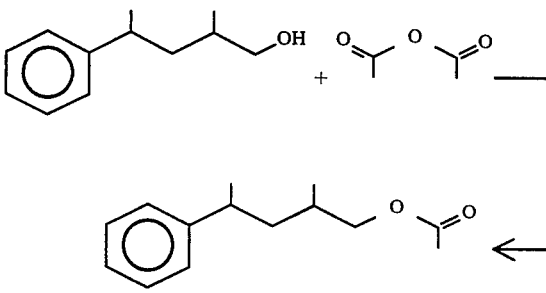

The esterification reaction is carried out in the presence of a protonic acid catalyst such as sulfuric acid, phosphoric acid or paratoluene sulfonic acid at a temperature in the range of from about 20° C. up to about 170° C. Preferably and conveniently the esterification reaction may be carried out at between 20° C. and 50° C. The mole ratio of acetic anhydride: alcohol defined according to the structure:

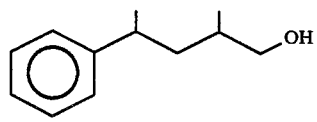

may vary from 2:1 up to 1:2 with a mole ratio of acetic anhydride:alcohol having the structure:

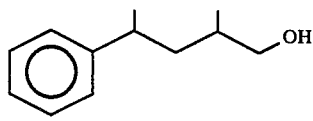

being preferred to be about 1:1. At the end of the reaction, the reaction mass is "worked-up" and the crude reaction product is fractionally distilled.

If it is attempted to carry out the foregoing hydrogenation reaction using a less active catalyst, e.g. supported palladium-on-carbon or a "Lindlar" catalyst such as supported palladium-on-calcium carbonate, a reaction whereby the compound:

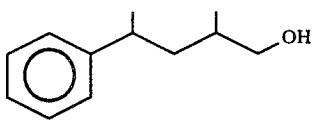

is formed will not take place but, instead, a reaction will take place thusly:

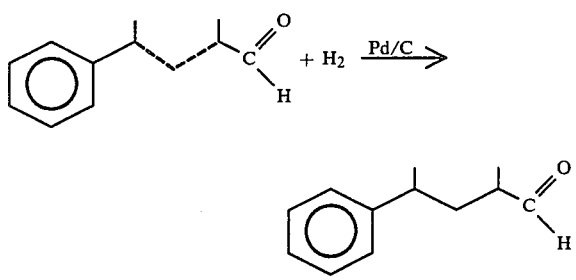

whereby the saturated aldehyde is formed. The creation of such unsaturated aldehyde is not desired in view of the intensely earthy aroma of same. Accordingly, the catalyst in the hydrogenation reaction is critical; that is, the reaction catalyst should be Raney nickel.

Specific examples of the methyl phenyl pentanol derivatives of our invention produced using the aforementioned process and their flavor and fragrance properties are as follows:

TABLE I

| Structure of Compound | Fragrance Aroma | Food Flavor |
|---|---|---|
| 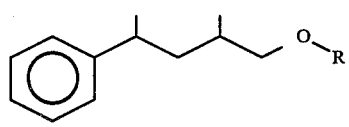 | A powerful, long-lasting stable green, grapefruit-like, nootkatone-like, animalic, leathery, vetiver-like, olibanum, musky and floral aroma profile. | A floral, green, weedy, fruity, grapefruit, galbanum-like aroma and taste at 1 ppm. |
| (acetate structure) | A green, styrallyl acetate-like aroma. | A floral, nootkatone-like, oriental, green pepper-like aroma and taste profile at 1 ppm. |

One or more of the aforementioned methyl phenyl pentanol derivatives defined according to the structure:

(structure with OR group)

wherein R is hydrogen or acetyl is useful as an olfactory agent and can be incorporated into a wide variety of compositions each of which will be enhanced or augmented by its green, grapefruit-like, nootkatone-like, animalic, leathery, vetiver-like, olibanum, musky and floral nuances.

The methyl phenyl pentanol derivatives individually or taken in combination, can be added to perfume compositions as pure compounds or can be added to mixtures of materials in fragrance imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the methyl phenyl pentanol derivatives of our invention is (are) useful as olfactory agent(s) and fragrance(s).

The term "perfume composition" is used herein to mean a mixture of compounds including, for example, natural essential oils, synthetic essential oils, alcohols (other than the alcohols of our invention), aldehydes, ketones, esters (other than the ester of our invention), lactones, nitriles and frequently hydrocarbons which are admixed so that the combined odors of the individual components produce a pleasant or desired fragrance. Such perfume compositions usually contain (a) the main note or "bouquet" or foundation stone of the composition, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials. Such perfume compositions of our invention can be used in conjunction with carriers, vehicles, solvents, dispersants, emulsifiers, surface active agents, aerosol propellants and the like.

In perfume compositions, the olfactory components contribute their particular olfactory characteristics but the overall effect of the perfume composition will be the sum of the effect of each ingredient. Thus, one or both of the methyl phenyl pentanol derivatives, of our invention can be used to alter, augment, modify or enhance the aroma characteristics of a perfume composition or a perfumed article, for example, by highlighting or moderating the olfactory reaction contributed by another ingredient of the composition.

The amount of one or both of the methyl phenyl pentanol derivatives of our invention which will be effective in perfume compositions depends upon many factors including the other ingredients, the amounts and the effects which are desired. It has been found that perfume compositions containing as much as 40% or as little as 0.005% by weight of the mixtures or compounds of this invention, or even less, can be used to impart a powerful, long-lasting, stable, green, grapefruit-like, nootkatone-like, animalic, leathery, vetiver-like, olibanum, musky and floral aroma to soaps, cosmetics and other products. The amount employed will depend upon considerations of cost, nature of the end product, the effect desired in the finished product and particular fragrance sought.

One or both of the methyl phenyl pentanol derivatives of our invention as disclosed herein can be used alone in a fragrance modifying composition or in a perfume composition as an olfactory component in detergents (e.g. anionic, cationic, nonionic or zwitterionic solid or liquid detergents) and soaps; space deodorants; perfumed plastics; perfume compositions; colognes, bath preparations such as bath oils, bath salts; hair preparations such as lacquers, brilliantines, pomades and shampoos; fabric softener compositions, fabric softener articles such as BOUNCE ® (manufactured by the Procter & Gamble Company of Cincinnati, Ohio), cosmetic preparations such as creams, powders, deodorants, hand lotions, sun screens, powders such as talcs, dusting powders, face powders and the like. When one or both of the methyl phenyl pentanol derivatives of our invention is used in perfumed articles such as the foregoing, it can be used in amounts of 0.01% or lower and generally it is preferred not to use more than about 2% in the finished perfumed article since the use of too much will tend to unbalance the total aroma and will needlessly raise the cost of the article. Thus, in summary, in perfumed articles, one or both of the methyl phenyl pentanol derivatives of our invention may be used in the range of from about 0.01% up to about 2.0%.

When one or both of the methyl phenyl pentanol derivatives of our invention are used as food flavor adjuvants, or are used to augment or enhance the flavor or aroma characteristics of foodstuffs, the nature of the co-ingredients included with said methyl phenyl pentanol derivatives in formulating the product composition will also serve to augment the organoleptic characteristics of the ultimate foodstuff treated therewith.

As used herein in regard to flavors, the term "augment" in its various forms means "supplying or imparting flavor, character or note to otherwise bland, relatively tasteless substances or augmenting the existing flavor characteristic wherein natural flavor is deficient in some regard or supplementing the existing flavor impression to modify its quality, character or taste".

As used herein in regard to food flavors, the term "enhance" is used to mean the intensification of a flavor or aroma characteristic or note without the modification of the quality thereof. Thus "enhancement" of a flavor or aroma means that the enhancement agent does not add any additional flavor note.

As used herein the term "foodstuff" includes both solids and liquids and ingestible materials or chewable but non-ingestible materials such as chewing gum. Such materials usually do, but need not have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with one or both of the methyl phenyl pentanol derivatives of our invention, non-reactive with one or both of the methyl phenyl pentanol derivatives of our invention and "ingestibly acceptable" and thus, non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g. sodium chloride, antioxidants, e.g. calcium and sodium ascorabate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g. mono- and diglycerides of fatty acids, skim milk powder, hexoses, pentoses, disaccharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium, peroxide, hydrogen peroxide and the like; starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate; texturizers, anticaking agents, e.g. aluminum calcium sulfate and tribasic calcium phosphate; enzymes; yeast foods, e.g. calcium lactate and calcium sulfate; nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid and 2-methyl-3-pentenoic acid; ketones and aldehydes, e.g. acetaldehyde, acetophenone, acetone, acetyl methyl carbinol, acrolein, n-butanal, crotonal, diacetyl, beta,beta-dimethylacrolein, n-hexanal, 2-hexenal, cis-3-hexenal, 2-heptanal, 4-(p-hydroxyphenyl)-2-butanone, alphaionone, beta-ionone, methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmin absolute, rose absolute, orris absolute, lemon essential oil, Bulgarian rose, yara yara, natural raspberry oil and vanilla; lactones; sulfides, e.g. methyl sulfide and other materials such as maltol, pulegone mercaptan, alpha-phellandrene, ethyl maltol, 2,2,4,4,6,6-hexamethyl-S-trithiane, acetoin and acetals, (e.g. 1,1-diethoxyethane, 1,1-dimethoxyethane and dimethoxymethane).

The specific flavoring adjuvant selected for use may be either solid or liquid depending upon the desired physical form of the ultimate product, i.e. foodstuff, whether simulated or natural, and should, in any event, be capable of providing an environment in which one or both of the methyl phenyl pentanol derivatives of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g. simulated foodstuffs, ingredients capable of providing normally solid compositions should be selected such as various cellulose derivatives.

As will be appreciated by those skilled in the art, the amount of one or both of the methyl phenyl pentanol derivatives of our invention employed in a particular instance can vary over a relatively wide range whereby to its desired organoleptic effects having reference to the nature of the product are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e. sufficient to alter the organoleptic characteristics of the parent composition, whether foodstuff per se or flavoring composition.

The use of insufficient quantities of one or both of the methyl phenyl pentanol derivatives of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of one or both of the methyl phenyl pentanol derivatives of our invention ranging from a small but effective amount, e.g. about 0.1 parts per million up to about 50 parts per million by weight based on total composition (more preferably, from about 0.2 ppm up to about 10 ppm) are suitable. Concentrations in excess of the maximum quantity slated are not normally recommended since they fail to prove commensurate with enhancement of organoleptic properties. In those instance wherein one or both of the methyl phenyl pentanol derivatives of our invention are added to the foodstuff as an integral component of a flavoring composition it is, of course, essential that the total quantity of flavoring composition employed be sufficient to yield an effective methyl phenyl pentanol derivative concentration in the foodstuff product.

Food flavoring compositions prepared in accordance with the present invention preferably contain one or both of the methyl phenyl pentanol derivatives of our invention in concentrations ranging from about 0.1% up to about 15% by weight based on the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or both of the methyl phenyl pentanol derivatives with, for example, gum arabic, gum tragacanth, carageenan and the like, and thereafter spray-drying the resultant mixture whereby to obtain the particular solid product. Pre-prepared flavor mixed in powder form, e.g. a fruit flavored powder mix, is obtained by mixing the dried solid components, e.g. starch, sugar and the like, and one or both of the methyl phenyl pentanol derivatives of our invention in a dry blender until the requisite degree of uniformity is achieved.

It is presently preferred to combine with one or both of the methyl phenyl pentanol derivatives of our invention the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene);
2-(4-hydroxy-4-methylpentyl) norbornadiene prepared according to U.S. application for Letters Patent Ser. No. 461,703 filed on Apr. 17, 1974, now U.S. Pat. No. 3,886,289;
Natural blackcurrant juice;
Buchu leaf oil;
Alpha-phellandrene;
Cis-3-hexen-1-ol;
Terpinenol-4;
Ethyl maltol;
Methyl benzoate;
Benzaldehyde;
Coriander oil;
α-ionone;
Ethyl heptanoate;
Methyl anthranilate;
Ethyl anthranilate;
Cinnamic alcohol;
Amyl valerinate;
Cinnamyl propionate;
Rhodinyl acetate;
Methyl β-hydroxy butyrate;
Ethyl β-hydroxy butyrate;
2-phenyl-3-carboethoxyfuran;
Cyclohexyl disulfide;

Grapefruit oil;
Nootkatone;
Bergamot oil;
Citral;
Amyl alcohol;
5-phenyl-4-pentenal;
5-phenyl-2-pentenal;
Allyl caproate;
2-(n-pentyl) thiazole;
2-(i-butyl) thiazole;
2-(i-propyl) thiazole;
2-(n-propyl) thiazole;
2-phenyl-4-pentenal;
2-phenyl-4-pentenaldimethylacetal;
Methional;
4-methylthiobutanal;
2-ethyl-3-acetylpyrazine;
Tetramethyl pyrazine;
2-methyl pyrazine;
trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thiobutanal-S-oxide;
Thioethanal-S-oxide;
Thiohexanal-S-oxide; and
Propyl propene thiosulfonate.

The following Examples I, III and IV are given to illustrate methods of preparing the methyl phenyl pentanol derivatives of our invention. The following Example II sets forth a method whereby the methyl phenyl pentanol derivatives of our invention cannot be produced. Examples V et seq. set forth methods for utilizing the methyl phenyl pentanol derivatives of our invention for their organoleptic properties. It will be understood that these examples are illustrative and the invention is not to be considered as restricted thereto except as indicated in the appended claims.

EXAMPLE I

Preparation of Dimethyl Phenyl Crotonaldehyde

Reaction:

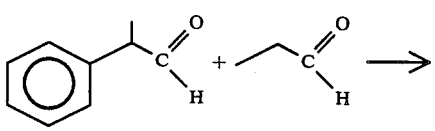

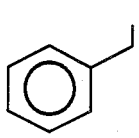

wherein in the resulting mixture, one of the dashed lines in each of the molecules represents a carbon-carbon double bond and the other of the dashed lines in each of the molecules represents a carbon-carbon single bond.

Into a 1,200 ml reaction flask equipped with stirrer, thermometer, a reflux condenser, nitrogen blanket apparatus and heating mantle is placed 500 grams of solid sodium hydroxide, 1,500 ml water and 5,000 ml methyl alcohol. The resulting mixture is cooled to 20° C. and over a period of ten minutes 1,340 grams of hydrotropic aldehyde defined according to the structure:

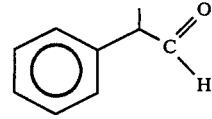

is added to the reaction mass. Over a period of six hours while maintaining the reaction temperature of 15°-23° C., 635 grams of n-propanal having the structure:

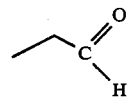

is added to the reaction mass. The reaction mass is then cooled to 15° C. The reaction mass is then stirred for 15 minutes at 15° C. 860 grams of glacial acetic acid is then slowly added to the reaction mass over a period of 15 minutes. The reaction mass is then mixed with 2 liters of 15% aqueous sodium chloride and the aqueous phase is separated from the organic phase. The aqueous phase weighs 1,568 grams. The aqueous phase is then distilled on a "Rushover" column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 30 | 100 | 150 | 114 |
| 2 | 104 | 140 | 2 | 200 |
| 3 | 108 | 160 | 2 | 236 |
| 4 | 133 | 188 | 2 | 178 |
| 5 | 133 | 205 | 2 | 233 |
| 6 | 100 | 230 | 2 | 225 |

The resulting product is then redistilled on a fractionation column to yield the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 66 | 120 | 2 | 9:1 | 42 |
| 2 | 68 | 127 | 2 | 9:1 | 37 |
| 3 | 75 | 131 | 2 | 9:1 | 41 |
| 4 | 108 | 132 | 2 | 9:1 | 41 |
| 5 | 105 | 133 | 2 | 9:1 | 39 |
| 6 | 105 | 133 | 2 | 9:1 | 46 |
| 7 | 32 | 128 | 2 | 9:1 | 20 |
| 8 | 100 | 133 | 2 | 9:1 | 44 |
| 9 | 101 | 138 | 2 | 9:1 | 46 |
| 10 | 104 | 139 | 2 | 9:1 | 39 |
| 11 | 103 | 145 | 2 | 9:1 | 33 |
| 12 | 103 | 160 | 2 | 9:1 | 32 |
| 13 | 130 | 220 | 2 | 9:1 | 36 |

Fractions 4–12 are bulked for subsequent reaction in Examples II and III.

Fractions 4–12 are compounds having the structures:

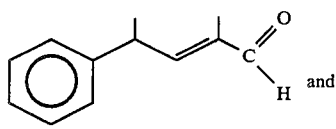 and

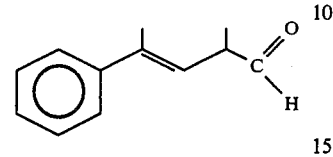

as confirmed by NMR, IR and mass spectral analyses.

Figure 1:
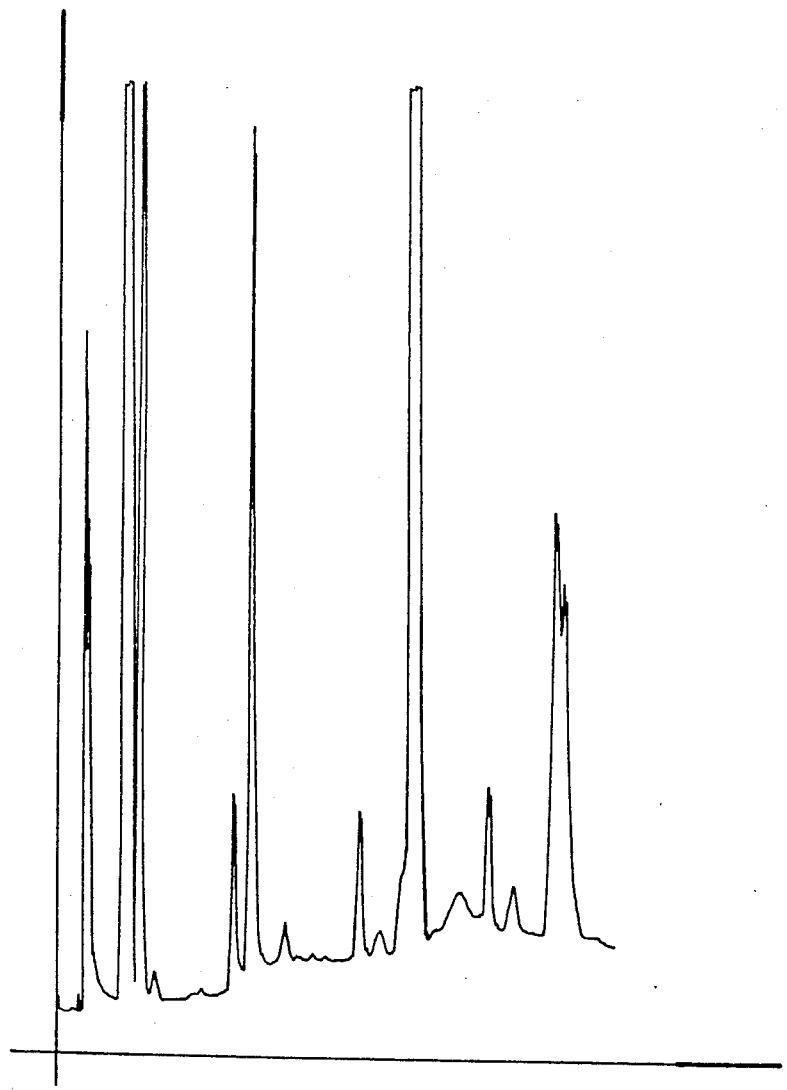
FIG. 1 is the GLC profile for the reaction product of Example I prior to distillation containing the compounds having the structures.

FIG. 1 is the GLC profile for the reaction product prior to distillation.

FIG. 2 is the NMR spectrum for bulked fractions 4–12 containing the compounds having the structures:

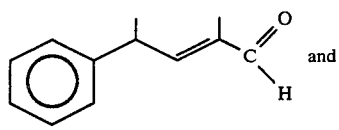 and

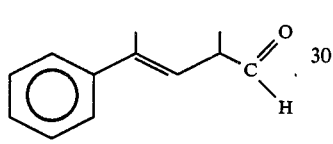

FIG. 3 is the infra-red spectrum for bulked fractions 4–12 of the foregoing distillation containing the compounds having the structures:

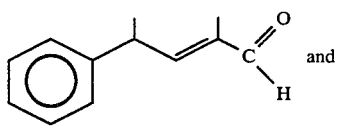 and

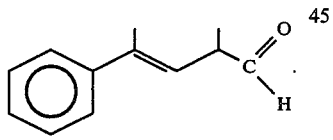

EXAMPLE II

Preparation of 2-Methyl-4-Phenyl Pentanal

Reaction:

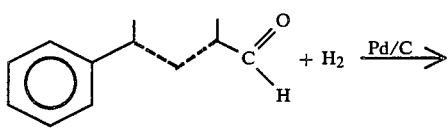 + $H_2$ $\xrightarrow{Pd/C}$

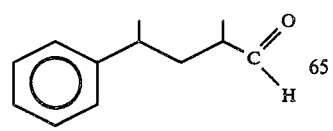

Into a Parr shaker container is placed 300 grams of bulked fractions 4–12 of the reaction product of Example I containing the compounds having the structures:

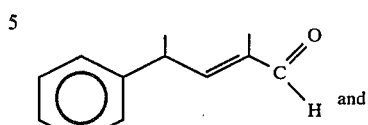 and

and 2 grams of 10% palladium supported on carbon. The shaker container is closed and is pressurized with hydrogen to 60 psig while maintaining the temperature thereof at 25°–35° C. The Parr shaker is operated at 59–60 psig at 25°–35° C. for a period of one hour. At the end of the one hour period, the contents of the Parr shaker container are emptied and filtered. The reaction product is then distilled yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 56/97 | 95/126 | 6 | 9:1 | 33 |
| 2 | 83 | 118 | 2 | 9:1 | 39 |
| 3 | 84 | 121 | 2.5 | 9:1 | 51 |
| 4 | 100 | 123 | 2.5 | 9:1 | 45 |
| 5 | 100 | 124 | 2.5 | 9:1 | 44 |
| 6 | 101 | 127 | 2.3 | 9:1 | 40 |
| 7 | 92 | 175 | 2 | 9:1 | 21 |

Fractions 4–6 are bulked and are found by NMR and IR analyses to contain the compound having the structure:

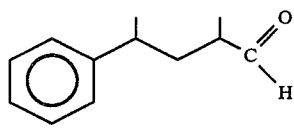

FIG. 4 is the NMR spectrum for bulked fractions 4–6 of the foregoing distillation. The resulting material has a green, floral, earthy aroma and is of no use in fragrances.

EXAMPLE III

Preparation of 2-Methyl-4-Phenyl Pentanol

Reaction:

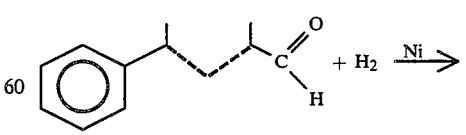 + $H_2$ $\xrightarrow{Ni}$

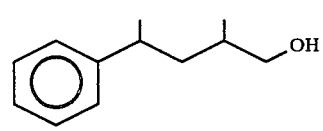

wherein in the compound containing the dashed lines, said compound represents a mixture and in each of the molecules of the mixture, one of the dashed lines represents a carbon-carbon double bond and the other of the dashed lines represents a carbon-carbon single bond.

Into a one-liter autoclave is placed 330 grams of bulked fractions 4–12 of the distillation product of Example I containing the compounds having the structures:

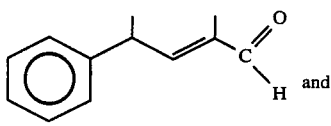

and

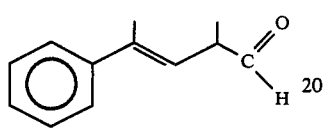

15 grams of Raney nickel and 330 grams of anhydrous isopropyl alcohol. The pressure in the autoclave is raised to 150 psig with hydrogen and the temperature of the contents of the autoclave is raised to 112° C. The autoclave is stirred for a period of fifteen hours at a temperature in the range of 98°–126° C. while maintaining the pressure at 150 psig. At the end of the fifteen hour period, the autoclave is depressurized and the contents are removed and filtered. The autoclave contents are then distilled yielding the following fractions:

| Fraction Number | Vapor Temp. (°C.) | Liquid Temp. (°C.) | Pressure mm/Hg |
|---|---|---|---|
| 1 | 43 | 100 | 150/4 |
| 2 | 123 | 160 | 3 |
| 3 | 192 | 167 | 3 |
| 4 | 141 | 175 | 3 |
| 5 | 167 | 220 | 3 |

The resulting distillate is refractionated yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 40/81 | 119/124 | 5/42 | 9:1 | 19 |
| 2 | 81 | 126 | 3.5 | 9:1 | 18 |
| 3 | 80 | 137 | 3.5 | 9:1 | 21 |
| 4 | 108 | 146 | 3.4 | 9:1 | 22 |
| 5 | 108 | 146 | 3.4 | 9:1 | 24 |
| 6 | 109 | 136 | 3.3 | 9:1 | 20 |
| 7 | 109 | 136 | 3.3 | 9:1 | 27 |
| 8 | 109 | 139 | 3.3 | 9:1 | 28 |
| 9 | 108 | 140 | 3.2 | 9:1 | 19 |
| 10 | 109 | 143 | 3.3 | 9:1 | 19 |
| 11 | 109 | 143 | 3.3 | 9:1 | 19 |
| 12 | 109 | 150 | 3.3 | 9:1 | 17 |
| 13 | 98 | 174 | 3.3 | 9:1 | 16 |
| 14 | 102 | 190 | 3.3 | 9:1 | 9 |

Fractions 9–12 are bulked for further evaluation as set forth in Examples V et seq. and are found by NMR and IR spectra to consist of the compound having the structure:

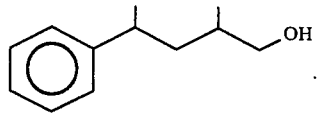

FIG. 5 is the NMR spectrum for bulked fractions 9–12 of the foregoing distillation.

FIG. 6 is the infra-red spectrum for bulked fractions 9–12 of the foregoing distillation.

EXAMPLE IV

Preparation of Acetate of 2-Methyl-4-Phenyl-1-Pentanol

Reaction:

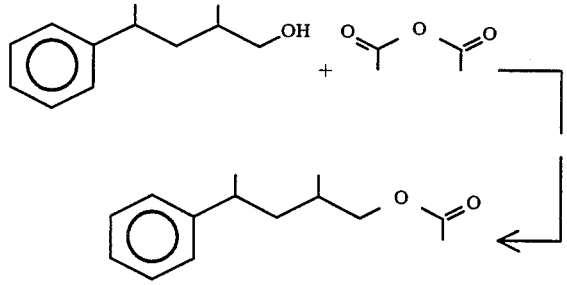

Into a 500 ml flask equipped with stirrer, thermometer, reflux condenser, heating mantle and addition funnel is placed 100 grams of acetic anhydride and 3.0 grams of phosphoric acid (concentrated). The resulting mixture is heated to 45° C. and over a period of 0.5 hours, 138 grams of bulked fractions 9–12 of the distillation product of Example III is added to the reaction mass from the addition funnel while maintaining the reaction temperature in the range of 35°–60° C. The reaction mass is heated at 45° C. with stirring for an additional three hours.

The reaction mass is then poured into one liter of water. 300 ml toluene is added to the reaction mass. The organic phase is separated from the aqueous phase and the aqueous phase is extracted with 200 ml of toluene. The toluene extract and the organic phase is combined and the combined phases are washed with 500 ml 10% aqueous sodium chloride. The organic phase is then washed with 500 ml 10% aqueous sodium carbonate followed by 500 ml saturated sodium chloride solution. The crude product weighs 569 grams and is distilled on a fractionation column yielding the following fractions:

| Fraction Number | Vapor Temp. (°C.) | Liquid Temp. (°C.) | Pressure mm/Hg |
|---|---|---|---|
| 1 | 103 | 120 | 1.8 |
| 2 | 93 | 110 | 1.8 |
| 3 | 93 | 110 | 1.8 |
| 4 | 91 | 118 | 1.8 |
| 5 | 96 | 170 | 1.8 |
| 6 | 96 | 220 | 1.8 |
| 7 | 96 | 121 | 1.8 |

Fractions 4–6 are bulked for subsequent evaluation in Examples V et seq.

NMR and IR analyses yield the information that bulked fractions 4–6 consist of the compound having the structure:

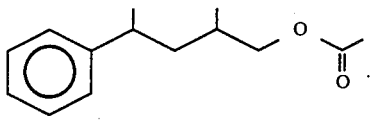

This compound has an interesting green, vegetative aroma from a fragrance standpoint and an interesting floral, nootkatone-like, oriental and green pepper aroma and taste from a food flavor standpoint.

FIG. 7 is the NMR spectrum for bulked fractions 4–6 of the foregoing distillation consisting of the compound having the structure:

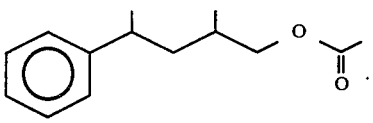

FIG. 8 is the infra-red spectrum for bulked fractions 4–6 of the foregoing distillation consisting of the compound having the structure:

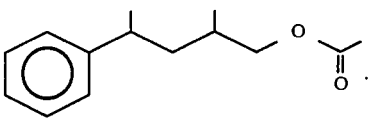

EXAMPLE V(A)

Impregnated Plastics and Air Fresheners

Scented polyethylene pellets having a pronounced green, floral, grapefruit-like, nootkatone-animalic, leathery, vetiver-like, olibanum and musky aromas are prepared as follows.

75 pounds of polyethylene having a melting point of about 220° F. is heated to about 230° F. in a container of the kind illustrated in FIGS. 9 and 10. 12.5 Pounds of 2-methyl-4-phenyl-1-pentanol (bulked fractions 9–12) prepared according to Example III, supra, are then quickly added to the liquified polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the 2-methyl-4-phenyl-pentanol-1-containing material through the orifices 234 (whereby such material exits through orifices 234). The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼″ in width ×3″ in length and employed in standard air freshening apparatus.

On operation of the standard air freshening apparatus is a room air freshener, after 4 minutes, the room has an aesthetically pleasing aroma as set forth, supra.

EXAMPLE V(B)

Treated Plastics and Air Freshener

100 Pounds of polypropylene are heated to about 300° F. 15 pounds of 2-methyl-4-pentanol acetate prepared according to Example IV (bulked fractions 4–6) are added to the liquified polypropylene. The procedure is carried out in the apparatus shown in FIGS. 9 and 10. After mixing for about 8 minutes, the valve "V" is opened to allow the exit of polypropylene mixture which has been treated with the phenylpentanol acetate, whereby solid pellets having pronounced aromas described as "green, vegetative, styrallyl acetate-like" are formed on the conveyor. The pellets thus obtained are then admixed with about 20 times their weight of unscented polypropylene and untreated polypropylene and the mixture is heated and molded into "spaghetti" tows. The "spaghetti" tows are cut into small cylinders approximately 0.1 inches in length ×0.2 inches in diameter. The cylinders have strong and pleasant aromas as described, supra.

The cylinders are used in standard air freshening apparatus to produce aesthetically pleasing aromas as set forth, supra with no foul odors in environments surrounding the air freshener apparatus.

A portion of the cylinders are ground into small particles to be used in the deodorant stick of Example V(C), supra,

EXAMPLE V(C)

Deodorant Stick

A deodorant stick composition is prepared containing the following materials:

| Ingredients | Parts by Weight |
| --- | --- |
| Propylene Glycol | 65.00 |
| Sodium stearate | 7.00 |
| Distilled water | 23.75 |
| IRGSAN ® DP-300 (2,4,4-trichlorol-2′-hydroxy diphenyl ether, manufactured by the Ciba Geigy Chemical Company and the trademark of the Ciba Geigy Chemical Company) | 0.25 |
| Ground polymer containing fragrance produced according to Example V(B), supra | 4.00 |

The ingredients combined without the ground polymer and heated to 75° C. These ingredients are mixed and continued to be heated until the sodium stearate has developed. The resulting mixture is cooled to 40° C. and the ground fragrance containing polymer is added and mixed at 40° C. until the suspension is formed. The resulting suspension is cooled and formed into sticks and the deodorant sticks exhibit a pleasant, fresh, green aroma when utilized in the axillary areas of a human being.

EXAMPLE VI

Grapefruit Flavor Formulation

The following formulation is prepared:

| Ingredients | Parts by Weight | |
|---|---|---|
| | Example VI(A) | Example VI(B) |
| Grapefruit oil | 92.0 | 92.0 |
| Bergamot oil | 2.0 | 2.0 |
| Citral | 3.0 | 3.0 |
| n-amyl alcohol | 1.0 | 1.0 |
| Ethyl acetate | 1.0 | 1.0 |
| 2-methyl-4-phenyl-1-pentanol (bulked fractions 9–12) prepared according to Example III | 1.5 | 0.0 |
| 2-methyl-4-phenyl-1-pentanol acetate (bulked fractions 4–6) produced according to Example IV | 0.0 | 1.8 |

When the above grapefruit formulations are added to water at the rate of 1%, an excellent grapefruit drink is prepared. The 2-methyl-4-phenyl-1-pentanol as well as the 2-methyl-4-phenyl-1-pentanol acetate give fruitier peeliness to the above two formulations thereby rendering each of them more desirable. The effect rendered by the 2-methyl-4-phenyl-1-pentanol and the 2-methyl-4-phenyl-1-pentanol acetate are "nootkatone"-like and, in addition, galbanum-like with excellent aesthetically pleasing red grapefruit notes.

When the above formulation is modified by adding to it 1.5 parts by weight of any of the following ingredients a yet more natural grapefruit peel aroma is imparted thereto:
(1,3-diethylacetonyl)(1,3-diisopropylacetonyl)sulfide
3-methyl-thio-4-heptanone
3-propyl-thio-4-heptanone
3-(methallylthio)-2,6-dimethyl-4-heptanone
3-crotylthio-2,6-dimethyl-4-heptanone
3-allylthio-2,6-dimethyl-4-heptanone.

EXAMPLE VII

A.

The following concentrate is prepared:

| Ingredients | Parts by Weight |
|---|---|
| Geraniol | 1.00 |
| Ethyl methyl phenyl glycidate | 3.50 |
| Nootkatone | 5.00 |
| Ethyl pelargonate | 5.00 |
| Isoamyl acetate | 4.00 |
| Vanillin | 2.00 |
| Isobutyl-2-methyl-pentenoate | 3.00 |
| 2-methyl-4-phenyl-1-pentanol | 1.00 |
| 2-methyl-4-phenyl-1-pentanol acetate | 1.13 |

B.

One volume of the concentrate prepared in Part "A", supra, is dissolved in four volumes of propylene glycol and the mixture is added to a hard candy melt at the rate of 1.5 ounces of the concentrate solution per 100 pounds of melt. After the finished candy has been produced, it is found to have an excellent grapefruit flavor. When the candy is compared with candy made under the same conditions but without either the 2-methyl-4-phenyl-1-pentanol or the 2-methyl-4-phenyl-1-pentanol acetate, it is found to have an inferior grapefruit flavor. Indeed, if only the 2-methyl-4-phenyl-1-pentanol or 2-methyl-4-phenyl-1-pentanol acetate is used, the grapefruit flavor is markedly superior than without either of the compounds.

EXAMPLE VIII

A. Powder Flavor Formulation

Twenty grams of the flavor formulation of Example VI is emulsified in a solution containing 300 grams gum acacia and 700 grams of water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| Liquid grapefruit flavor of Example VI | 20 |
| Propylene glycol | 9 |
| Cab-O-Sil ® M-5 (Brand of silica produced by the Cabot Corporation of 125 High St. Boston, Mass. 02110; Physical properties: Surface area: 200 m²/gram Nominal particle size: 0.012 microns Density: 2.3 lbs/cu. ft. | 5 |

The Cab-O-Sil ® is dispersed in a liquid grapefruit flavor composition of Example VI with vigorous stirring thereby resulting in a viscous liquid. 71 parts by weight of the powder flavor composition of Part "A", supra, is then blended into said viscous liquid with stirring at 25° C. for a period of thirty minutes resulting in a dry, free-flowing, sustained release grapefruit flavored powder.

EXAMPLE IX

Ten parts by weight of 50 Bloom pigskin gelatin is added to ninety parts by weight of water at a temperature of 150° C. The mixture is agitated until the gelatin is completely dissolved and the solution is cooled to 120° F. Twenty parts by weight of the liquid grapefruit flavor composition of Example VI is added to the solution which is them homogenized to form an emulsion having a particle size typically in the range of 5–40 microns. The material is kept at 120° F. under which conditions the gelatin will not jell.

Coacervation is induced by adding slowly and uniformly forty parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of a 7% aqueous solution of sodium sulfate at 65° F. The resulting jelled coacervate may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE X

Chewing Gum

One hundred parts by weight of chicle are mixed with four parts by weight of the flavor prepared in accordance with Example VIII. Three hundred parts of sucrose and one hundred parts of corn syrup are added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant, long-lasting grapefruit flavor.

EXAMPLE XI

Chewing Gum

One hundred parts by weight of chicle are mixed with eighteen parts by weight of the flavor prepared in accordance with Example IX. Three hundred parts of sucrose and one hundred parts of corn syrup are then added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant, long-lasting grapefruit flavor.

EXAMPLE XII

Toothpaste Formulation

The following separate groups of ingredients are prepared:

| Parts by Weight | Ingredient |
| --- | --- |
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example VIII |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized and finally tubed.

The resulting toothpaste, when used in a normal toothbrushing procedure, yields a pleasant grapefruit flavor of constant strong intensity throughout said procedure (1–1.5 minutes).

EXAMPLE XIII

Chewable Vitamin Tablets

The flavor material produced according to the process of Example IX is added to a chewable vitamin tablet formulation at the rate of ten grams per kilogram which chewable vitamin tablet formulation is prepared as follows:

In a Hobart mixer, the following materials are blended to homogeneity:

| Ingredients | Grams/ 1000 tablets |
| --- | --- |
| Vitamin C (ascorbic acid) as ascorbic acid-sodium ascorbate mixture 1:1 | 70.110 |
| Vitamin B$_1$ (thiamine mononitrate) as Rocoat ® thiamine mononitrate 33⅓% (Hoffman La Roche) | 4.000 |
| Vitamin B$_2$ (riboflavin) as Rocoat ® riboflavin 33⅓% | 5.000 |
| Vitamin B$_6$ (pyridoxine hydrochloride) as Rocoat ® phridoxine hydrochloride 33⅓% | 4.000 |
| Niacinamide as Rocoat ® niacinamide 33⅓% | 33.000 |
| Calcium pantothenate | 11.500 |
| Vitamin B$_{12}$ (cyanocobalamin) as Merck 0.1% in gelatin | 3.500 |
| Vitamin E (dl-alpha tocopheryl acetate) as dry Vitamin E acetate 33⅓% | 6.600 |
| d-Biotin | 0.044 |
| Flavor of Example IX | (as indicated above) |
| Certified lake color | 5.000 |
| Sweetener, sodium saccharin | 1.000 |
| Magnesium stearate lubricant | 10.000 |
| Mannitol q.s. to make | 500.000 |

Preliminary tablets are prepared by slugging with flat-faced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong grapefruit flavor for a period of 12 minutes.

EXAMPLE XIV

Chewing Tobacco

Onto 100 pounds of tobacco for chewing (85% Wisconsin leaf and 15% Pennsylvania leaf) the following casing is sprayed at the rate of 30%:

| Ingredients | Parts by Weight |
| --- | --- |
| Corn syrup | 60.00 |
| Licorice | 10.00 |
| Glycerine | 20.00 |
| Fig juice | 4.60 |
| Prune juice | 5.00 |
| 2-methyl-4-phenyl-1-pentanol | 0.04 |

The resultant product is re-dried to a moisture content of 20%. On chewing, this tobacco has an excellent substantially consistent, long-lasting grapefruit-like nuance in conjunction with the tobacco notes.

EXAMPLE XV

Herbal Perfume Formulation

The following mixtures are prepared:

| Ingredients | Parts by Weight Example XV(A) | Parts by Weight Example XV(B) |
|---|---|---|
| Oakmoss absolute (50% in diethyl phthalate) | 20 | 20 |
| Alpha-methyl-3,4-methylene-dioxyhydrocinnamic aldehyde | 10 | 10 |
| Methyl dihydrojasmonate | 100 | 100 |
| Coumarin | 20 | 20 |
| Musk ketone | 80 | 80 |
| Isocyclocitral (10% in diethyl phthalate) | 10 | 10 |
| Galbanum oil (10% in diethyl phthalate) | 6 | 6 |
| Rosemary oil | 10 | 10 |
| Pine needle oil | 60 | 60 |
| Fir balsam absolute (10% in diethyl phthalate) | 10 | 10 |
| Bergamot oil | 60 | 60 |
| Lemon oil | 14 | 14 |
| Benzyl acetate | 468 | 468 |
| Linalool | 80 | 80 |
| Indole (10% in diethyl phthalate) | 6 | 6 |
| Undecalactone (10% in diethyl phthalate) | 12 | 12 |
| 2-methyl-4-phenyl-1-pentanol (bulked fractions 9–12) produced according to Example III | 12 | 0 |
| 2-methyl-4-phenyl-1-pentanol acetate (bulked fractions 4–6) produced according to Example IV | 0 | 20 |

The addition to this herbal formulation of the 2-methyl-4-phenyl-1-pentanol imparts to this herbal formulation an excellent green, floral, grapefruit-like, nootkatone-like, animalic, leathery, vetiver-like, olibanum and musky undertone. In general, the formulation can be described as "herbal with green, floral, grapefruit-like, nootkatone-like, animalic, leathery, vetiver-like, olibanum, and musky undertones".

When the 2-methyl-4-phenyl-1-pentanol acetate is added to this herbal formulation, the herbal formulation is imparted with green, vegetative topnotes. Thus, the formulation of Example XV(B) can be described as "herbal with green and vegetative topnotes".

EXAMPLE XVI

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| 2-methyl-4-phenyl-1-pentanol (bulked fractions 9–12) produced according to Example III | A green, floral, grapefruit-like, nootkatone, animalic, leathery, vetiver-like, olibanum, and musky aroma. |
| 2-methyl-4-phenyl-1-pentanol acetate (bulked fractions 4–6) produced according to Example IV | A green, vegetative, styrallyl acetate-like aroma profile. |
| The fragrance formulation of Example XV(A) | An herbal aroma with green, floral, grapefruit-like, nootkatone-like, animalic, leathery, vetiver-like, olibanum and musky undertones. |
| The fragrance formulation of Example XV(B) | An herbal aroma with green and vegetative topnotes. |

EXAMPLE XVII

Perfumed Liquid Detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table II of Example XVI are prepared containing 0.10%, 0.15%, 0.20%, 0.25%, 0.30% and 0.35% of the substance set forth in Table II of Example XVI. They are prepared by adding and homogeneously mixing the appropriate quantity of substance set forth in Table II of Example XVI in the liquid detergent. The detergents all possess excellent aromas as set forth in Table II of Example XVI, the intensity increasing with greater concentrations of substance as set forth in Table II of Example XVI.

EXAMPLE XIX

Preparation of Colognes and Handkerchief Perfumes

Compositions as set forth in Table II of Example XVI are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XVI are imparted to the colognes and to the handkerchief perfumes at all levels indicated.

EXAMPLE XX

Preparation of Soap Compositions

One hundred grams of soap chips (per sample) (IVORY ®, produced by the Procter & Gamble Company of Cincinnati, Ohio), are each mixed with one gram samples of substances as set forth in Table II of Example XVI until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table II of Example XVI.

EXAMPLE XXI

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol ® 45- (a $C_{14}$—$C_{15}$ alcohol ethoxylanted with 11 moles of ethylene oxide) | 12 |

| Ingredient | Percent by Weight |
|---|---|
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example XVI. Each of the degergent samples has an excellent aroma as indicated in Table II of Example XVI.

EXAMPLE XXII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and ther perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
57% $C_{20-22}$ HAPS
22% isopropyl alcohol
20% antistatic agent
1% of one of the substances as set forth in Table II of Example XVI.

Fabric softening compositions prepared according to Example I at column 15 of U.S. Pat. No. 3,632,396 having aroma characteristics as set forth in Table II of Example XVI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XVI is admixed in each case with the outer coating mixture, thereby providing a total aromatized outer coating weight ratio to substrate of about 0.5:1 by weight of the substrate. The aroma characteristics are imparted in a pleasant manner to the head space in a dryer or operation thereof in each case using said drier-added fabric softener non-woven fabrics and these aroma characteristics are described in Table II of Example XVI, supra.

EXAMPLE XXIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example XVI, supra | 0.10 weight percent |

The perfuming substances as set forth in Table II of Example XVI add aroma characteristics as set forth in Table II of Example XVI which are rather intense and aesthetically pleasing to the users of the soft-feel, good-hold pump hair sprays.

EXAMPLE XXIV

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A and COMPOSITION B are then mixed in a 50:50 weight ratio of A:B and cooled to 45° C. and 0.3 weight percent of perfuming substance as set forth in Table II of Example XVI is added to the mixture. The resulting mixture is cooled to 40° C. and blending is carried out for an additional one hour in each case. At the end of this blending period, the resulting material has a pleasant fragrance as indicated in Table II of Example XVI.

What is claimed is:
1. A process for augmenting or enhancing the aroma of a consumable material selected from the group consisting of perfume compositions, colognes and perfumed articles comprising the step of adding to said consumable material an aroma augmenting or enhancing quantity of a 2-methyl-4-phenyl-1-pentanol derivative defined according to the structure:

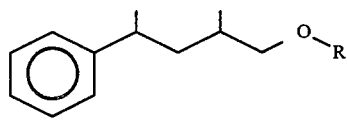

wherein R is hydrogen or acetyl.
2. The process of claim 1 wherein in the 2-methyl-4-phenyl-1-pentanol derivative, R is hydrogen.
3. The process of claim 1 wherein in the 2-methyl-4-phenyl-1-pentanol derivative, R is acetyl.
4. The process of claim 1 wherein the consumable material is a perfumed article and the perfumed article is a solid or liquid anionic, cationic, nonionic or zwitterionic detergent.
5. The process of claim 1 wherein the consumable material is a perfumed article and the perfumed article is a fabric softener composition or a fabric softener article.
6. The process of claim 1 wherein the consumable material is a perfume composition or a cologne.
7. The process of claim 1 wherein the consumable material is a perfumed polymer.

* * * * *